(12) United States Patent
Okuno

(10) Patent No.: US 10,555,714 B2
(45) Date of Patent: Feb. 11, 2020

(54) X-RAY IMAGING DEVICE

(71) Applicant: Shimadzu Corporation, Kyoto (JP)

(72) Inventor: Tomoharu Okuno, Kyoto (JP)

(73) Assignee: Shimadzu Corporation,
Nishinokyo-Kuwabaracho, Nakagyo-ku,
Kyoto-shi, Kyoto (JP)

(*) Notice: Subject to any disclaimer, the term of this patent is extended or adjusted under 35 U.S.C. 154(b) by 210 days.

(21) Appl. No.: 15/718,541

(22) Filed: Sep. 28, 2017

(65) Prior Publication Data
US 2019/0090839 A1 Mar. 28, 2019

(51) Int. Cl.
*A61B 6/00* (2006.01)
*A61B 6/10* (2006.01)
*A61B 6/06* (2006.01)

(52) U.S. Cl.
CPC ............... *A61B 6/542* (2013.01); *A61B 6/06* (2013.01); *A61B 6/10* (2013.01); *A61B 6/4464* (2013.01)

(58) Field of Classification Search
None
See application file for complete search history.

(56) References Cited

U.S. PATENT DOCUMENTS

| | | | | |
|---|---|---|---|---|
| 2015/0055752 A1* | 2/2015 | Takahashi | ................ | H04N 5/32 378/62 |
| 2015/0223767 A1* | 8/2015 | Sehnert | .................... | A61B 6/06 378/42 |
| 2019/0099150 A1* | 4/2019 | Konkle | ................. | A61B 6/587 |

FOREIGN PATENT DOCUMENTS

| JP | 2008-117641 | 5/2008 |
|---|---|---|
| JP | 2010279516 A | 12/2010 |
| JP | 2013070723 A | 4/2013 |
| JP | 2013-135390 | 7/2013 |
| JP | 5344807 B | 11/2013 |

OTHER PUBLICATIONS

JPO Notification of Reasons for Refusal for related Patent Application No. JP 2015-053638, dated Apr. 12, 2018 (machine translation).

* cited by examiner

*Primary Examiner* — Yara B Green
(74) *Attorney, Agent, or Firm* — Muir Patent Law, PLLC

(57) ABSTRACT

Provided is an X-ray imaging apparatus capable of properly performing an automatic exposure control and an appropriately performing X-ray imaging control with a simple configuration. In cases where there exists a plurality of AEC photo pickup fields for automatic exposure, based on the positional information on an X-ray irradiation area and the AEC photo pickup field(s), the presence or absence of AEC photo pickup field(s) where all areas of the sensitive area are not included in the X-ray irradiation area is detected. In cases where there exist one or more AEC photo pickup fields not included in the X-ray irradiation area, the corresponding AEC photo pickup field is set to be unused. As a result, it is possible to appropriately perform an automatic exposure control and/or perform an X-ray imaging control appropriately with a simple structure.

15 Claims, 3 Drawing Sheets

X-RAY IMAGING DEVICE

FIELD OF THE INVENTION

The present invention relates to an X-ray imaging apparatus that performs X-ray imaging, and more particularly to a technique of an automatic exposure control that automatically and optimally controls an exposure of X-ray imaging.

BACKGROUND ART

An X-ray imaging apparatus is equipped with an X-ray generator, an X-ray tube, an X-ray tube holder that holds the X-ray tube so as to be suspended from a ceiling or holds the X-ray tube above a floor, a collimator (X-ray diaphragm) that controls an X-ray irradiation area from the X-ray tube by a leaf, and an X-ray detector (an X-ray film, a CR (Computed Radiography) or an FPD (Flat Panel Detector)) that detects X-rays. A subject is held by using an X-ray imaging stand (a table or a stand), and X-ray imaging is performed by accommodating the aforementioned X-ray detector in the X-ray image capturing stand. In cases where the X-ray detector is an FPD, the X-ray image (X-ray captured image) captured from the FPD is transmitted to a digital device connected to the FPD and displayed on the monitor of the digital device (see, for example, Japanese Patent No. 5,344,807).

In the collimator that controls the X-ray irradiation area from the X-ray tube by a leaf, the irradiation field of the rectangular X-ray formed by the collimator can be adjusted in the length of the two sides by, for example, a longitudinal dimension adjustment knob and a lateral dimension adjustment knob provided on the panel surface of the collimator. However, doing this adjustment while monitoring the subject on the X-ray imaging stand by irradiating X-rays to the subject before the X-ray imaging results in an increased subject exposure.

Therefore, in order to prevent such exposure, the collimator normally has a built-in irradiation field lamp which becomes a light source and has a function of irradiating light instead of X-rays. It is possible to adjust the position and size of the irradiation field before imaging without irradiating X-rays by confirming the irradiation field of light adjusted so as to match the irradiation field of X-rays. The light irradiation start or irradiation termination is performed by a light irradiation button. For example, each time the light irradiation button is pressed, irradiation start and irradiation termination are alternately repeated.

An operator such as a technician adjusts the adjustment knob of the collimator to confirm the X-ray irradiation area corresponding to the imaging site of the subject by the irradiation field of light. After that, the operator instructs the subject not to move the body, leaves the examination room surrounded by a material (such as lead) that does not transmit X-rays, and presses the X-ray imaging button of the X-ray generator to perform the imaging.

In the meantime, an X-ray imaging apparatus equipped with an automatic exposure control (AEC: Auto Exposure Control) that automatically and optimally controls the exposure of X-ray imaging is widely used (see, for example, Japanese Patent No. 5344807, Japanese Unexamined Patent Application Publication No. 2008-117641 and Japanese Unexamined Patent Application Publication No. 2013-135390, the disclosure of each of these documents being incorporated by reference in their entirety). This automatic exposure control (AEC) is a control in which a part of the X-ray (transmitted X-ray) that has passed through a subject is detected in a specific detection range (hereinafter referred to as "photo pickup field") and the detected X-ray is converted into an electric signal (X-ray output signal), and when the integrated value of the electric signal (X-ray output signal) reaches an appropriate value, the X-ray is interrupted. By performing this AEC, the integrated quantity (incident dose) of the transmitted X-ray irradiated to the X-ray detector is set to an appropriate value, which in turn can obtain a desired luminance signal (pixel value).

Normally, in an X-ray imaging apparatus equipped with an AEC, an exposure control detection unit (AEC detection unit) is installed on the subject side of a Bucky stand (imaging table) that holds an X-ray detector. There is a plurality of photo pickup fields of the installed AEC detection unit, and photo pickup fields suitable for the imaging site are selected for each imaging. For example, in FIG. 2 and FIG. 3 of Japanese Unexamined Patent Application Publication No. 2008-117641 (incorporated by reference in its entirety), there exist three photo pickup fields (photo pickup field right side, photo pickup field center, and photo pickup field left side). During the X-ray imaging, when the incident dose of the X-ray incident on the selected AEC photo pickup field becomes equal to or larger than a predetermined value, the X-ray is immediately cut off.

Also, in Japanese Patent No. 5,344,807 (incorporated by reference in its entirety), an X-ray output signal is controlled in proportion to the area (effective area) in which the X-ray irradiation area in the photo pickup field (AEC photo pickup field) of the AEC detection unit is set. Even when the X-ray dose is reduced by the collimator, by controlling the X-ray output signal in proportion to the effective area, the incident dose to the X-ray detector can always be kept constant.

When an X-ray detector represented by an FPD or the like also serves as an AEC detection unit, compared with image detection pixels, in the detection pixels in the AEC detection unit, the accumulation operation time becomes shortened by the amount of time for the dose detection operation. As a result, compared with an image detection pixel, in the detection pixel in the AEC detection unit, the pixel value becomes small, casing image quality deterioration. Under the circumstances, in Japanese Unexamined Patent Application Publication No. 2013-135390 (incorporated by reference in its entirety), it has been proposed that the pixel value at the detection pixel is corrected so as to become the same as the pixel value at the image detection pixel.

SUMMARY

However, even in the case of a conventional example having such a configuration, there is a problem that an automatic exposure control (AEC) is not properly performed and therefore an exposure increases. That is, as in a conventional method, when an operator performs X-ray imaging by adjusting the irradiation field (X-ray irradiation area) of the X-ray while confirming the irradiation field of light, a problem arises in which a subject or the like becomes a shadow, and therefore as shown in FIG. 4, the sensitive areas (effective areas) of the photo pickup fields $V_C$, $V_L$, and $V_R$ become not actually included in the X-ray irradiation area $V_I$ (in FIG. 4, a part of the sensitive area of the photo pickup field $V_R$ becomes not included in the X-ray irradiation area $V_I$). As a result, there is a possibility that the sensitive area (effective area) of the preset photo pickup field decreases.

Along with this, the X-ray incident dose incident on the AEC photo pickup field per unit time decreases by the blocked area, the time (arrival time) required for the X-ray output to reach the prescribed predetermined X-ray total incident dose for blocking is prolonged. As a result, the X-ray total incident dose output to the subject increases, causing an unnecessary exposure to the subject. Similarly, the X-ray total incident dose increases for the region of the detection pixel by the X-ray detector by the aforementioned arrival time extends, so it becomes an X-ray captured image in which the density (pixel value) is difference in each region, resulting in an image that is difficult to diagnose. Even if multiple AEC photo pickup fields are subjected to be used, there may be some cases where the sensitive area of at least one of the AEC photo pickup fields is decreased for the reasons described above.

Furthermore, X-ray imaging may not be performed at a position where the sensitive area of the AEC photo pickup field is usually reduced, and the position of the X-ray irradiation area with respect to the X-ray detector is performed in a predetermined positional relationship in imaging positioning. Therefore, in cases where imaging is performed even at a position that reduces the sensitive area of the AEC photo pickup field, the position of the X-ray irradiation area with respect to the X-ray detector in the imaging position is different from usual, and therefore there is a possibility of mistaking imaging positioning. Further, there is a possibility that the output/display position of the X-ray captured image changes accordingly.

Further, in Japanese Patent No. 5344807, as described above, although it is disclosed that the X-ray output signal is controlled in proportion to the area where the X-ray irradiation area in the AEC photo pickup field is set, a multiplier that multiplies by a proportional value (1/Y assuming ratio Y) is additionally required. As the set area decreases, the value of X-ray output signal after multiplication (1/Y) increases, and therefore there is a possibility that the value saturates in the comparative detector that receives this output signal. As a result, there is a possibility that an effective X-ray detection output cutoff is not performed and the exposure to the subject is increased.

In the correction based on the ratio of the effective area in Japanese Patent No. 5344807, there is also a problem that the X-ray irradiation area itself cannot be accurately determined by the scattered rays of the subject and an accurate correction is not performed. In any case, the X-ray irradiation area itself cannot be accurately obtained, and as a result there is a possibility that an automatic exposure control (AEC) cannot be performed properly.

The disclosed embodiments been made in view of such circumstances, and aims to provide an X-ray imaging apparatus capable of properly performing an automatic exposure control and appropriately performing an X-ray imaging control with a simple structure.

An X-ray imaging apparatus according to embodiments the present invention is an X-ray imaging apparatus for performing X-ray imaging, and in some embodiments includes X-ray irradiation means configured to irradiate an X-ray toward a subject, photo pickup field setting means configured to select a photo pickup field among a plurality of photo pickup fields for an automatic exposure and set a selected photo pickup field, lighting field detection means configured to detect presence or absence of a photo pickup field in which all areas of a sensitive area are not included in an X-ray irradiation area based on positional information of the X-ray irradiation area irradiated by the X-ray irradiation means and the sensitive area of the photo pickup field, and unused setting means configured to set photo pickup field(s) to be unused when there exist one or more photo pickup fields not included in the X-ray irradiation area.

In cases where there exists a plurality of photo pickup fields for an automatic exposure, based on the positional information of the sensitive area of the X-ray irradiation area and the photo pickup field, the lighting field detection means detects the presence or absence of the photo pickup field(s) in which all areas of the sensitive area are not included in the X-ray irradiation area. In cases where photo pickup field(s) are not included in the X-ray irradiation area, the sensitive area is decreased and there exist one or more photo pickup fields (i.e., photo pickup fields with a reduced sensitive area) not included in the X-ray irradiation area, and the unused setting means sets the applicable photo pickup field(s) to be unused. Then, (1) the photo pickup field other than the photo pickup field(s) set to be unused is selected from the photo pickup field selected by the photo pickup field setting means, or (2) the photo pickup field setting means selects and sets the photo pickup field other than the photo pickup field(s) set to be unused. If an automatic exposure control and an X-ray imaging control are performed using the remaining photo pickup fields without using the photo pickup field(s) in which the sensitive area is reduced, as described above, in the remaining photo pickup fields, the total X-ray incident dose necessary for cutting off the X-ray output is cut off at the predetermined value. Therefore, an appropriate automatic exposure control can be performed, which in turn can perform an appropriate X-ray imaging control, and the density (pixel value) of the X-ray captured image (X-ray image) obtained by imaging becomes constant. In some examples, it is unnecessary to accurately obtain the X-ray irradiation area by the scattered rays of the subject, and/or there is no need to perform a correction as described in Japanese Patent No. 5344807, and a multiplier may not be necessary. As a result, it is possible to appropriately perform an automatic exposure control with a simple structure and perform an X-ray imaging control appropriately.

Further, an X-ray imaging apparatus for performing X-ray imaging according to a disclosed embodiment includes X-ray irradiation means configured to irradiate an X-ray toward a subject, lighting field detection means configured to detect presence or absence of a photo pickup field in which all areas of a sensitive area are not included in an X-ray irradiation area based on positional information on the X-ray irradiation area irradiated by the X-ray irradiation means and a sensitive area of the photo pickup field for an automatic exposure, and warning means configured to issue a warning when a photo pickup field not included in the X-ray irradiation area exists.

While there exists a plurality of photo pickup fields utilized in some embodiments, but in other embodiments, the X-ray imaging apparatus may also be applicable to the case where there exists only one photo pickup field. Based on the positional information of the X-ray irradiation area and the sensitive area of the photo pickup field, the lighting field detection means detects the presence or absence of the photo pickup field in which all areas of the sensitive area are not included in the X-ray irradiation area. As described in the function and effect of the former embodiments, the sensitive area is decreased in the photo pickup field not included in the X-ray irradiation area. In the latter embodiments, in cases where there exists a photo pickup field (i.e., a photo pickup field with a reduced sensitive area) that is not included in the X-ray irradiation area, the aforementioned warning means issues a warning. By issuing a warning to an operator by the warning means before X-ray imaging, it is understood that the X-ray irradiation area is deviated or missing from the sensitive area of the photo pickup field before the X-ray imaging. Therefore, when the operator is re-adjusted the position of the subject and/or the X-ray irradiation area, the appropriate X-ray total incident dose is incident on the photo pickup field. Therefore, an appropriate automatic exposure control can be performed, which in turn can perform an appropriate X-ray imaging control, and the density (pixel value) of the X-ray captured image (X-ray image) obtained by imaging becomes constant. At this time, since the operator can recognize in advance that the positioning of imaging is different from usual, it is possible to correct when there is mispositioning of imaging, and the output/display position of the X-ray captured image (X-ray Image) does not change. Furthermore, by the readjustment, the X-ray output signal from the photo pickup field may be the same as that in the prior art, and the multiplier as disclosed in Japanese Patent No. 5344807 may be unnecessary. As a result, it is possible to appropriately perform an automatic exposure control and perform an X-ray imaging control appropriately with a simple structure.

Further, features of the different embodiments may be combined for yet further embodiments. For example, when embodiments implement use of plural photo pickup fields and there exists a photo pickup field not included in the X-ray irradiation area, warning means that issues a warning is provided in the same manner as described in latter embodiments. As described above, in cases where there exists a plurality of photo pickup fields, when there exist one or more photo pickup fields not included in the X-ray irradiation area, even when setting the corresponding photo pickup field to be unused, a warning may be given to an operator with the warning means before the X-ray imaging. Then, the operator readjusts the position of the subject and/or the X-ray irradiation area so that an appropriate X-ray total incident dose is incident on the photo pickup field which was set to be unused, so that the photo pickup field which was set to be unused is set to be usable.

The warning means may issue a warning with light, or may issue a warning with sound. Further, the warning may be performed by combining both light and sound. For example, it may be configured such that the warning is normally performed with light and the warning is performed with sound at the stage before the X-ray imaging.

The warning means may perform the warning at the timing when the X-ray imaging operation is performed. That is, when there exists a photo pickup field not included in the X-ray irradiation area, at that time the warning means does not issue a warning and, for example, only a detection flag is set by the lighting field detection means, and the warning is issued based on the detection flag at the timing when the X-ray imaging operation is performed. Also in this case, the warning means may issue a warning with light, or may issue a warning with sound.

An X-ray collimator means for restricting the area irradiated by X-ray irradiation means may be provided, and the positional information of the X-ray irradiation area may be calculated based on the respective positional information of the X-ray irradiation means, the X-ray collimator means, and the X-ray detection means (for detecting the X-ray that transmitted through the subject). In this manner, that the X-ray irradiation area may be set to which position of the X-ray detection means is calculated. Then, the X-ray irradiation area is used for detecting the presence or absence of the photo pickup field (not included in the X-ray irradiation area) in the lighting field detection means.

Further, the relative position information storage means for storing the relative position information of the sensitive area of the photo pickup field and the X-ray detection means (for detecting the X-rays that passed through the subject) may be provided, and the relative position information is referred to, based on the positional information of the X-ray detection means. Thus, the positional information of the sensitive area of the photo pickup field may be calculated. Thus, the positional information of the sensitive area of the photo pickup field may be calculated by referring to the relative position information based on the positional information of the X-ray detection means. The X-ray irradiation area may be used for detecting the presence or absence of the photo pickup field (not included in the X-ray irradiation area) in the lighting field detection means.

Accordingly, in cases where there exists a plurality of photo pickup fields for an automatic exposure, based on the positional information on the X-ray irradiation area and the sensitive area of the photo pickup field, the lighting field detection means detects the presence or absence of the photo pickup field in which all areas of the sensitive area are not included in the X-ray irradiation area. In cases where there exist one or more photo pickup fields not included in the X-ray irradiation area, the unused setting means is set the corresponding photo pickup field to be unused. As a result, it is possible to appropriately perform an automatic exposure control and perform an X-ray imaging control appropriately with a simple structure.

Further, based on the positional information of the X-ray irradiation area and the sensitive area of the photo pickup field, the lighting field detection means may detect the presence or absence of the photo pickup field in which all areas of the sensitive area are not included in the X-ray irradiation area. When there exists a photo pickup field not included in the X-ray irradiation area, a warning means may issue a warning. By issuing a warning to an operator by the warning means before X-ray imaging, it is understood that the X-ray irradiation area is deviated or missing from the sensitive area of the photo pickup field before the X-ray imaging. Thus, the operator can readjust the position of the subject and/or the X-ray irradiation area. As a result, it is possible to appropriately perform an automatic exposure control and perform an X-ray imaging control appropriately with a simple structure.

DETAILED DESCRIPTION

Figure 1:
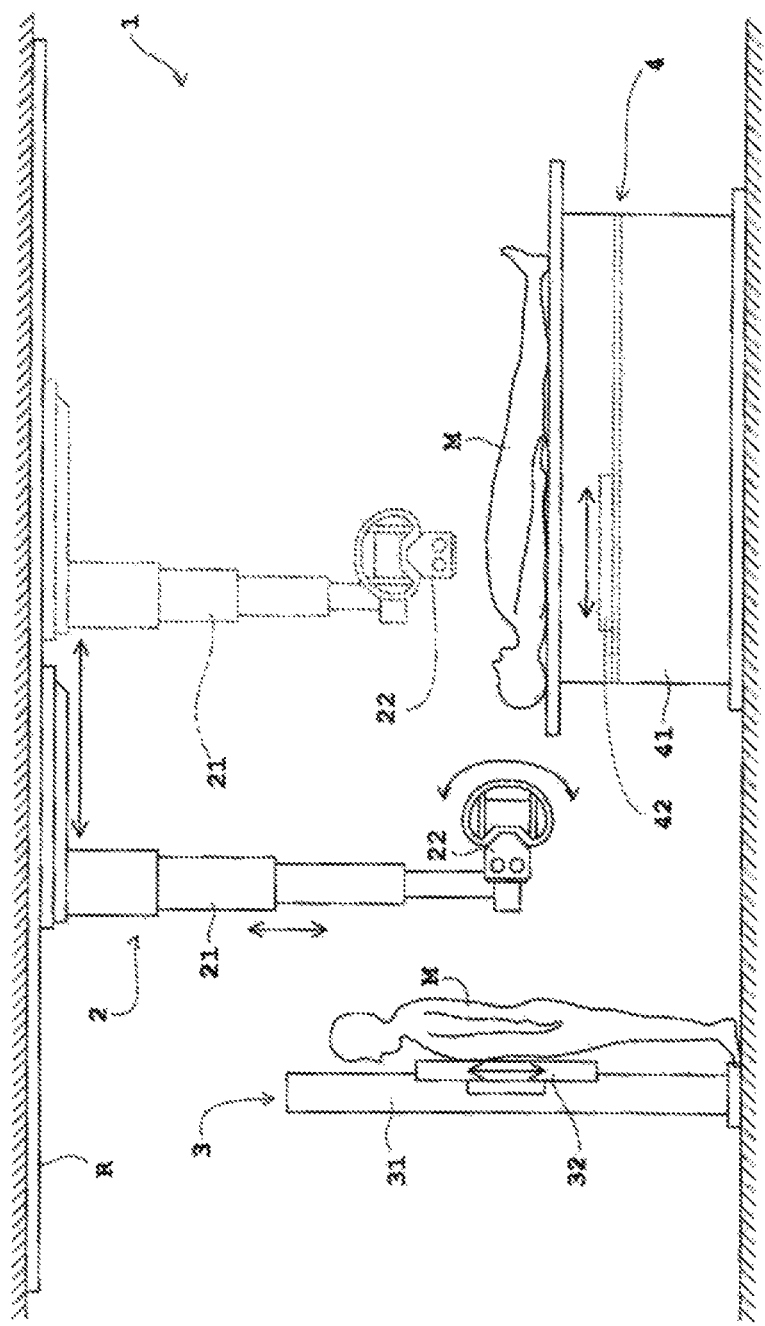
FIG. 1 is a schematic diagram of an X-ray imaging apparatus according to exemplary embodiments.

Hereinafter, some embodiments embodying the present invention will be described with reference to the drawings, in which various exemplary embodiments are shown. The invention may, however, be embodied in many different forms and should not be construed as limited to the exemplary embodiments set forth herein. These example exemplary embodiments are just that—examples—and many embodiments and variations are possible that do not require the details provided herein. It should also be emphasized that the disclosure provides details of alternative examples, but such listing of alternatives is not exhaustive. Furthermore, any consistency of detail between various exemplary embodiments should not be interpreted as requiring such detail—it is impracticable to list every possible variation for every feature described herein. The language of the claims should be referenced in determining the requirements of the invention.

Ordinal numbers such as "first," "second," "third," etc. may be used simply as labels of certain elements, steps, etc., to distinguish such elements, steps, etc. from one another. Terms that are not described using "first," "second," etc., in the specification, may still be referred to as "first" or "second" in a claim. In addition, a term that is referenced with a particular ordinal number (e.g., "first" in a particular claim) may be described elsewhere with a different ordinal number (e.g., "second" in the specification or another claim).

The embodiments are described, and illustrated in the drawings, in terms of functional blocks, units and/or modules. These blocks, units and/or modules may be physically implemented by electronic (or optical) circuits such as logic circuits, discrete components, microprocessors, hard-wired circuits, memory elements, wiring connections, and the like, which may be formed together in a single integrated circuit (e.g., as a single semiconductor chip) or as separate integrated circuits and/or discrete components (e.g., several semiconductor chips wired together on a printed circuit board) using semiconductor fabrication techniques and/or other manufacturing technologies. These blocks, units and/or modules may be implemented by a processor (e.g., a microprocessor, a controller, a CPU, a GPU) or processors that are programmed using software (e.g., microcode) to perform various functions discussed herein. Each block, unit and/or module may be implemented by dedicated hardware, or as a combination of dedicated hardware to perform some functions and a processor to perform other functions. Also, each block, unit and/or module of the embodiments may be embodied by physically separate circuits and need not be formed as a single integrated circuit.

Example 1

Figure 2:
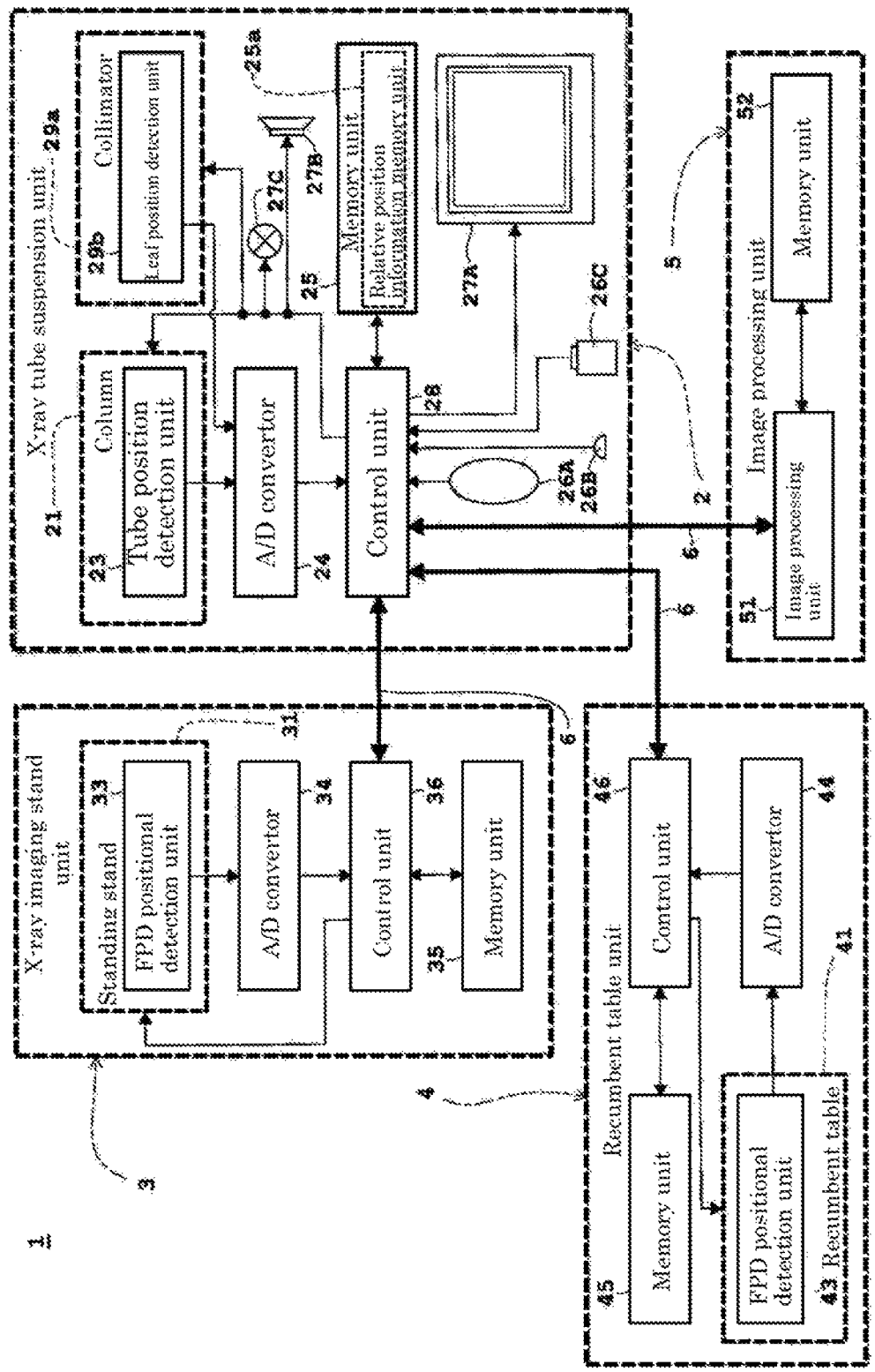
FIG. 2 is a block diagram of the X-ray imaging apparatus according to exemplary embodiments.

Hereinafter, Example 1 of the present invention will be described with reference to the drawings. FIG. 1 is a schematic diagram of an X-ray imaging apparatus according to each Example, and FIG. 2 is a block diagram of the X-ray imaging apparatus according to each Example. As with Example 2, which will be described later, in this Example 1, a flat panel type X-ray detector (FPD: Flat Panel Detector) will be described as an example for the X-ray detection means.

As with Example 2 which will be described later, as shown in FIG. 1, the X-ray imaging apparatus 1 according to Example 1 is equipped with an X-ray tube suspension unit 2 suspends and supports the X-ray tube 22 so that the X-ray tube 22 is movable along the ceiling, an X-ray imaging stand unit 3 which performs X-ray imaging of the subject M in a standing posture state, a recumbent table unit 4 configured to perform X-ray imaging of a subject M in a recumbent posture, and an image processing unit 5 (not shown in FIG. 1) configured to perform image processing on the X-ray image of the subject M. As shown in FIG. 2, the X-ray tube suspension unit 2, the X-ray imaging stand unit 3, the recumbent table unit 4, and the image processing unit 5 are electrically connected to each other by communication cables 6. The X-ray tube suspension unit 2, the X-ray imaging stand unit 3, the recumbent table unit 4, and the image processing unit 5 are configured to communicate with each other by the communication cables 6.

As shown in FIG. 1, the X-ray tube suspension unit 2 is provided with a column 21 capable of moving along the ceiling and vertically expandable and retractable, and an X-ray tube 22 supported by the column 21 and capable of adjusting its orientation. Further, as shown in FIG. 2, the X-ray tube suspension unit 2 is provided with a tube position detection unit 23 for detecting the position and angle of the X-ray tube 22, and an A/D converter 24 for converting the analog voltage of the positional information obtained by the tube position detection unit 23 and the leaf position detection unit 29b into digital data. Other than the above, the X-ray tube suspension unit 2 is provided with a memory unit 25, an input unit 26 (a pointing device 26A, an AEC photo pickup field selection button 26B, an X-ray imaging button 26C), an output unit 27 (a display unit 27A, a buzzer 27B, a warning lamp 27C), a control unit 28, a collimator 29a, and a leaf position detection unit 29b. In this example, the X-ray tube 22 corresponds to the X-ray irradiation means, the AEC photo pickup field selection button 26B corresponds to the photo pickup field setting means, the control unit 28 corresponds to the lighting field detection means and the unused setting means, and the collimator 29a corresponds to the X-ray collimator means.

As shown in FIG. 1, the X-ray imaging stand unit 3 is equipped with an upright stand 31 that supports a subject M in a standing posture and a flat panel type X-ray detector (FPD) 32 mounted on the upright stand 31 in a vertically movable manner. Further, as shown in FIG. 2, the X-ray imaging stand unit 3 is equipped with an FPD position detection unit 33 for detecting the position of the FPD 32 and an A/D converter 34 for converting the analog voltage of the positional information obtained by the FPD position detection unit 33 into digital data. Other than the above, the X-ray imaging stand unit 3 is equipped with a memory unit 35 and a control unit 36. In the same manner as in the X-ray tube suspension unit 2, the X-ray imaging stand unit 3 may be equipped with an input unit and an output unit. Further, the control unit 28 of the X-ray tube suspension unit 2 may directly control the FPD 32 of the X-ray imaging stand unit 3 without providing the memory unit 35 and the control unit 36 in the X-ray imaging stand unit 3. The FPD 32 of the X-ray imaging stand unit 3 and the FPD 42 of the recumbent table unit 4, which will be described later, corresponds to the X-ray detection means in some examples.

As shown in FIG. 1, the recumbent table unit 4 is equipped with a recumbent table 41 for placing the subject M in a recumbent posture and a flat panel type X-ray detector (FPD) 42 mounted on the recumbent table 41 in a horizontally movable manner. As shown in FIG. 2, the recumbent table unit 4 is equipped with an FPD position detection unit 43 for detecting the position of the FPD 42 and an A/D converter 44 for converting the analog voltage of the positional information obtained by the FPD position detection unit 43 into digital data. Other than the above, the recumbent table unit 4 is equipped with a memory unit 45 and a control unit 46. In the same manner as in the X-ray tube suspension unit 2, the recumbent table unit 4 may be equipped with an input unit and an output unit. Further, the control unit 28 of the X-ray tube suspension unit 2 may directly control the FPD 42 of the recumbent table unit 4 without equipping the memory unit 45 and the control unit 46 in the recumbent table unit 4.

As shown in FIG. 2, the image processing unit 5 is equipped with an image processing unit 51 for creating an X-ray image (X-ray captured image) by performing image processing based on the X-ray output signal obtained by the FPD 32 of the X-ray imaging stand unit 3 or the FPD 42 of the recumbent table unit 4. Other than the above, the image processing unit 5 is equipped with a memory unit 52 that writes and stores an X-ray image. In the same manner as in the X-ray tube suspension unit 2, the image processing unit 5 may be equipped with an input unit and an output unit. Further, it may be configured such that an X-ray image is written and stored in the memory unit 25 of the X-ray tube suspension unit 2 without equipping the memory unit 52 in the image processing unit 5.

The column 21 of the X-ray tube suspension unit 2 is movable along the rail R mounted along the ceiling. The rail R is also mounted along the depth direction of the paper of FIG. 1, so that the column 21 is movable along the depth direction. The column 21 is configured to be extendable and contractible and support the X-ray tube 22, so that the X-ray tube 22 is horizontally/vertically movable. Further, the orientation of the X-ray tube 22 is adjustable. Accordingly, it is possible to perform X-ray imaging in a standing posture by adjusting the orientation of the X-ray tube 22 by moving horizontally/vertically as shown by the solid line in FIG. 1 toward the upright stand 31 of the X-ray imaging stand unit 3. Furthermore, it is also possible to perform X-ray imaging in a recumbent posture by adjusting the orientation of the X-ray tube 22 by moving the X-ray tube 22 horizontally/vertically as shown by the two-dot chain line in FIG. 1 toward the recumbent table 41 of the recumbent table unit 4.

As shown in FIG. 2, a tube position detection unit 23 is attached to the column 21 supporting the X-ray tube 22, and the position and angle of the X-ray tube 22 are detected by the tube position detection unit 23. The tube position detection unit 23 is configured by, for example, a potentiometer, and the resistance value of the potentiometer changes as the X-ray tube 22 moves or rotates, and the output voltage changes with respect to the reference voltage according to the resistance value. This output voltage is an analog voltage, and the analog voltage of the positional information (including the angle) obtained by the potentiometer is sent to the A/D converter 24. The A/D converter 24 converts the analog voltage into digital data.

In addition to the positional information of the sensitive area of the photo pickup field (AEC photo pickup field), the memory unit 25 of the X-ray tube suspension unit 2 writes and stores the respective positional information of the X-ray tube 22, the collimator 29a, the FPD 32 of the X-ray imaging stand unit 3, and the FPD 42 of the recumbent table FPD 42 and the positional information of the X-ray irradiation area, and reads out as necessary, via the control unit 28. In particular, the memory unit 25 is equipped with a relative position information memory unit 25a, and the relative position information between the sensitive area of the AEC photo pickup field and the FPD 32 of the X-ray imaging stand unit 3 or the FPD 42 of the recumbent table unit 4 is written in advance and stored. The control unit 28 calculates the positional information of the sensitive area of the AEC photo pickup field by referring to the relative position information based on the positional information of the FPD 32 and 42, and writes the positional information of the sensitive area of the calculated photo pickup field and stores it in the memory unit 25. The memory unit 25 of the X-ray tube suspension unit 2, the memory unit 35 of the X-ray imaging stand unit 3, the memory unit 45 of the recumbent table unit 4, and the memory unit 52 of the image processing unit 5 are configured by a storage medium represented by, e.g., a ROM (Read-only Memory) and a RAM (Random-Access Memory).

The input unit 26 of the X-ray tube suspension unit 2 sends data and instructions entered by an operator to the control unit 28. The pointing device 26A of the input unit 26 is a mouse, a keyboard, a joystick, a track ball, a touch panel, etc. Other than the above, in cases where there exists a plurality of photo pickup fields (AEC photo pickup fields) for an automatic exposure, the AEC photo pickup field selection button 26B of the input unit 26 is a button that selects AEC photo pickup fields to use and sets the selected AEC photo pickup field. The operator presses the AEC photo pickup field selection button 26B and selects AEC photo pickup fields to use. The number of AEC photo pickup fields to be selected may be plural. The X-ray imaging button 26C of the input unit 26 is a button for performing an X-ray imaging operation. For example, the X-ray imaging button 26C is configured by a two-step switch, the button is half pressed to heat the tube of the X-ray tube 22, and the button is fully pressed to prepare the X-ray irradiation.

The display unit 27A of the output unit 27 of the X-ray tube suspension unit 2 is composed of a monitor, etc. Other than the above, the buzzer 27B of the output unit 27 is configured to issue a warning with sound, and the warning lamp 27C of the output unit 27 is configured to issue a warning with light. Further, the display unit 27A may be configured by a touch panel mounting the aforementioned AEC photo pickup field selection button 26B, and this touch panel may be attached to the X-ray tube 22. In this way, the function of the input unit 26 may be provided in the output unit 27.

The control unit 28 of the X-ray tube suspension unit 2 totally controls each part constituting the X-ray tube suspension unit 2. The control unit 28 of the X-ray tube suspension unit 2, the control unit 36 of the X-ray imaging stand unit 3, the control unit 46 of the recumbent table unit 4, and the image processing unit 51 of the image processing unit 5 are configured by a central processing unit (CPU), etc. In Example 1, the control unit 28 has a function of performing an automatic exposure control on the X-ray image processed by the image processing unit 51, which will also be applied to Example 2 to be described later. Further, in Example 1, the control unit 28 has a function of lighting field detection means for detecting the presence or absence of an AEC photo pickup field in which all areas of the sensitive area are not included in the X-ray irradiation area based on the positional information of the X-ray irradiation area and the sensitive area of the AEC photo pickup field, and in cases where there exist one or more AEC photo pickup fields not included in the X-ray irradiation area, a function of unused setting means that sets the corresponding AEC photo pickup field to be unused.

The collimator 29a of the X-ray tube suspension unit 2 is configured to limit the area irradiated by the X-ray tube 22. Specifically, the collimator 29a is composed of four leaves (not shown) arranged vertically and horizontally, and is configured to control (the size of) the irradiation field of a rectangular X-ray surrounded by four leaves by adjusting each leaf vertically and horizontally. The leaf position detection unit 29b is provided in the collimator 29a, and the leaf position detection unit 29b detects the leaf position and the opening degree information (the size of the opening surrounded by the four leaves) of the collimator 29a. In the same manner as in the tube position detection unit 23 of the X-ray tube suspension unit 2, the leaf position detection unit 29b is also composed of a potentiometer. The resistance value of the potentiometer changes as the leaf moves, and according to the resistance value, the output voltage changes. This output voltage is an analog voltage. The analog voltage of the positional information obtained by the potentiometer is sent to the A/D converter 24, and the A/D converter 24 converts the analog voltage into digital data. As described in the "Background Art" section, it may be configured such that the irradiation field lamp (not shown) is embedded in the housing of the collimator 29a so as to confirm the irradiation field of light before X-ray imaging.

As shown in FIG. 1, the upright stand 31 of the X-ray imaging stand unit 3 is installed on the floor surface. The FPD 32 of the X-ray imaging stand unit 3 is capable of moving upward and downward along the upright stand 31. On the other hand, the recumbent table 41 of the recumbent table unit 4 is also installed on the floor surface. The FPD 42 of the recumbent table unit 4 is capable of horizontally moving within the recumbent table 41.

In Example 1, the FPD 32 of the X-ray imaging stand unit 3 and the FPD 42 of the recumbent table unit 4 share an AEC detection unit, which will also be applied to Example 2 which will be described later. That is, when an X-ray image is acquired by the FPD 32 of the X-ray imaging stand unit 3 or the FPD 42 of the recumbent table unit 4, the X-ray detected in the area of the FPD matching the AEC photo pickup field is converted into an electric signal (X-ray output signal). When the integrated value of this electric signal (X-ray output signal) reaches an appropriate value, the X-ray irradiation is interrupted. As a result, an automatic exposure (AEC) is performed by the FPD.

As shown in FIG. 2, the FPD position detection unit 33 is provided in the FPD 32 of the X-ray imaging stand unit 3, so that the FPD position detection unit 33 detects the position of the FPD 32. On the other hand, the FPD position detection unit 43 is also provided in the FPD 42 of the recumbent table unit 4, so that the FPD position detection unit 43 detects the position of the FPD 42. In the same manner as in the FPD position detection unit 23 and the leaf position detection unit 29b of the X-ray tube suspension unit 2, the FPD position detection unit 33 of the X-ray imaging stand unit 3 and the FPD position detection unit 43 of the recumbent table unit 4 are also composed of a potentiometer. The resistance value of the potentiometer changes in accordance with the movement of the FPD 32 and 42, so that the output voltage changes with respect to the reference voltage in accordance with the resistance value. This output voltage is an analog voltage, and the analog voltage of the positional information obtained by the potentiometer is sent to the A/D converter 34 in the case of the X-ray imaging stand unit 3, and is sent to the A/D converter 44 in the case of the recumbent table unit 4. The A/D converter 34 and 44 converts the analog voltage into respective digital data. Further, the analog voltage of the positional information obtained by the potentiometer of the X-ray imaging stand unit 3 and the recumbent table unit 4 is also sent to the X-ray tube suspension unit 2 via the communication cable 6.

The memory unit 35 of the X-ray imaging stand unit 3 writes and stores the upper end position and the lower end position of the FPD 32 in the X-ray imaging and reads out as necessary. On the other hand, the memory unit 45 of the recumbent table unit 4 writes and stores the left end position and the right end position of the FPD 42 in the X-ray imaging and reads out as necessary.

The control unit 36 of the X-ray imaging stand unit 3 totally controls each part constituting the X-ray imaging stand unit 3, and the control unit 46 of the recumbent position table unit 4 totally controls each part constituting the recumbent table unit 4.

The control unit 28 of the X-ray tube suspension unit 2 and the control unit 36 of the X-ray imaging stand unit 3 are electrically connected by a communication cable 6. The control unit 28 of the X-ray tube suspension unit 2 and the control unit 46 of the recumbent table unit 4 are electrically connected by a communication cable 6. The control unit 28 of the X-ray tube suspension unit 2 and the image processing unit 51 of the image processing unit 5 are electrically connected by a communication cable 6. By connecting as described above, the X-ray tube suspension unit 2, the X-ray imaging stand unit 3, the recumbent table unit 4, and the image processing unit 5 are configured to be able to communicate with each other. Other than the above, each control unit 28, 36, and 46 drivingly controls the X-ray tube 22 and the FPD 32 and 42, and each control unit 28, 36, and 46 controls a motor (not shown), thereby drivingly controlling the motor of the X-ray tube 22 and the FPD 32 and 42. By driving the motor, it is possible to control the X-ray tube 22 and the FPD 32 and 42 to desired positions and adjust the orientation of the X-ray tube 22 at a desired angle.

Figure 3:
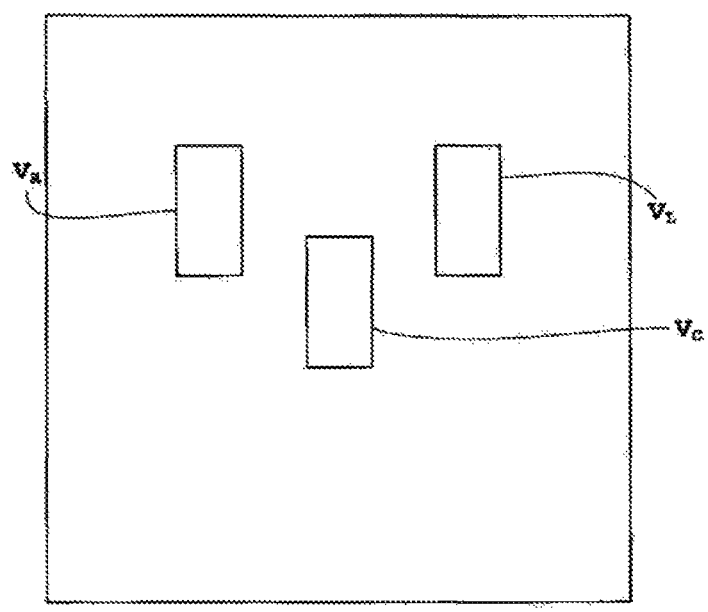
FIG. 3 is a schematic diagram of a position of an AEC photo pickup field.
Figure 4:
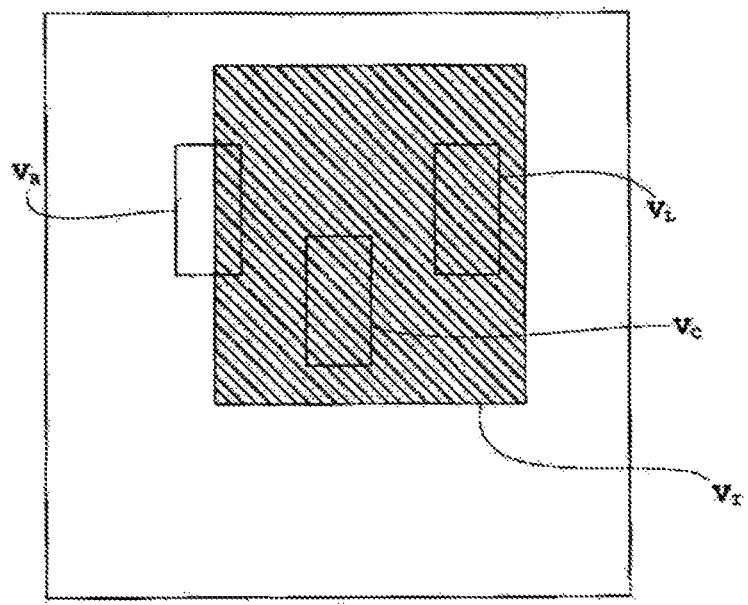
FIG. 4 is a schematic diagram of the AEC photo pickup field and an X-ray irradiation area.

Next, setting (selection) of the AEC photo pickup field, detection of the AEC photo pickup field, and unused setting of the AEC photo pickup field will be described with reference to FIGS. 3 and 4. FIG. 3 is a schematic diagram of the position of the AEC photo pickup field, and FIG. 4 is a schematic diagram of the AEC photo pickup field and the X-ray irradiation area. In FIGS. 3 and 4, X-ray imaging with the upright stand 31 (see FIGS. 1 and 2, not shown in FIGS. 3 and 4) will be described as an example.

First, the relative position information between the sensitive area of the AEC photo pickup field and the FPD 32 (see FIG. 1) installed along the upright stand 31 is written in the relative position information memory unit 25a (see FIG. 2) of the X-ray tube suspension unit 2 in advance. In cases where the FPD 32 also serves as the AEC detection unit as in Example 1, it is not always necessary to previously store the relative position information between the sensitive area of the AEC photo pickup field and the FPD 32, which will also be applied to Example 2 to be described later.

The operator presses the AEC photo pickup field selection button 26B (see FIG. 2) of the X-ray tube suspension unit 2. For example, as shown in FIG. 3, the position of the central photo pickup field is denoted as $V_C$, the position of the photo pickup field on the left side is denoted as $V_L$, and the position of the photo pickup field on the right side is denoted as $V_R$. The operator presses the AEC photo pickup field selection button 26B to select an AEC photo pickup field (photo pickup field $V_C$, $V_L$, $V_R$ in FIG. 3) to be used. The information of the selected AEC photo pickup field is sent to the control unit 28 (see FIG. 2) of the X-ray tube suspension unit 2. It should be noted that the left and right are directions viewed from the subject M (see FIG. 1), not the direction viewed from the operator.

The control unit 28 calculates the positional information of the X-ray irradiation area $V_I$ shown in FIG. 4 based on the positional information of the X-ray tube 22 (see FIG. 1) obtained by tube position detection unit 23 of the X-ray tube suspension unit 2 (see FIG. 2), the positional information of the collimator 29a (see FIG. 2) obtained by the leaf position detection unit 29b (see FIG. 2) of the X-ray tube suspension unit 2, and the positional information on the FPD 32 obtained by the FPD position detection unit 33 (see FIG. 2) of the X-ray imaging stand unit 3. With this, it is calculated which position of the FPD 32 the X-ray irradiation area $V_I$ is irradiated and set.

The control unit 28 calculates the positional information of the sensitive area of the AEC photo pickup field by referring to the relative position information based on the positional information of the current FPD 32 (obtained by the FPD position detection unit 33) with reference to the relative position information memory unit 25a that stores the relative position information between the sensitive area of the AEC photo pickup field and the FPD 32. Furthermore, in the AEC photo pickup field set by the AEC photo pickup field selection button 26B, the control unit 28 referrers to the positional information of the X-ray irradiation area $V_I$ calculated based on the positional information, etc., of the FPD 32, as described above, the positional information of the FPD 32 of the sensitive area (photo pickup fields $V_C$, $V_L$, and $V_R$ in FIGS. 3 and 4) of the AEC photo pickup field calculated based on the positional information of the FPD 32.

With this, in the AEC photo pickup field set by the AEC photo pickup field selection button 26B, based on the positional information of the sensitive area of the X-ray irradiation area $V_I$ and the AEC photo pickup field, the presence or absence of the AEC photo pickup field in which all areas of the sensitive area are not included in the X-ray irradiation area $V_I$ is detected. In FIG. 4, in the center AEC photo pickup field $V_C$ and the left AEC photo pickup field $V_L$, all areas of the sensitive area are included in the X-ray irradiation area $V_I$. However, a part of the sensitive area is not included in the X-ray irradiation area $V_I$ only in the right side of the AEC photo pickup field $V_R$. Therefore, in FIG. 4, the control unit 28 detects the AEC photo pickup field $V_R$ in which all areas of the sensitive area are not included in the X-ray irradiation area $V_I$ based on the positional information of the X-ray irradiation area $V_I$ and the sensitive area of the AEC photo pickup field.

In cases where there exist one or more AEC photo pickup field in which all areas of the sensitive area are not included in the X-ray irradiation area $V_I$, the control unit 28 sets the corresponding AEC photo pickup field to be unused. In FIG. 4, the AEC photo pickup field $V_R$ in which all areas of the sensitive area are not included in the X-ray irradiation area $V_I$ is set to be unused.

According to the X-ray imaging apparatus of Example 1 having the aforementioned configuration, in cases where there exists a plurality of AEC photo pickup fields for an automatic exposure as in Example 1, based on the positional information of the sensitive area of the X-ray irradiation area and the AEC photo pickup field, the control unit 28 detects the presence or absence of the AEC photo pickup field in which all areas of the sensitive area are not included in the X-ray irradiation area. In cases where in the AEC photo pickup field not included in the X-ray irradiation area, the sensitive area is decreased and there exist one or more AEC photo pickup fields (i.e., the AEC photo pickup fields with a reduced sensitive area) not included in the X-ray irradiation area, the control unit 28 sets the corresponding AEC photo pickup field to be unused. Then, from the AEC photo pickup field set (selected) by the AEC photo pickup field selection button 26B, the AEC photo pickup field other than the AEC photo pickup field set to be unused is selected and set. If an automatic exposure control and an X-ray imaging control are performed using the remaining AEC photo pickup fields without using the AEC photo pickup field in which the sensitive area is reduced as described above, in the remaining AEC photo pickup fields, the X-ray total incident dose necessary for cutting off the X-ray output is cut off at the predetermined value. Therefore, an appropriate automatic exposure control can be performed, which in turn can perform an appropriate X-ray imaging control, and the density (pixel value) of the X-ray captured image (X-ray image) obtained by imaging becomes constant. Further, it may not be necessary to accurately obtain the X-ray irradiation area by the subject M's scattered rays, and as described herein, there is no need to correct as described in Japanese Patent 5344807, and multiplier may become unnecessary. As a result, it is possible to appropriately perform an automatic exposure control and perform an X-ray imaging control appropriately with a simple structure.

In Example 1, a collimator 29a for limiting the area irradiated by the X-ray tube 22 is provided. The positional information of the X-ray irradiation area is calculated based on the respective positional information of the X-ray tube 22, the collimator 29a, and the flat panel type X-ray detector (FPD) (for detecting the X-ray that transmitted through the subject M) (FPD 32 in the case of X-ray imaging at the upright stand 31). In this manner, it is calculated that which position of the FPD 32 the X-ray irradiation area is set. Then, the X-ray irradiation area is used for detecting the presence or absence of the AEC photo pickup field (not included in the X-ray irradiation area) in the control unit 28.

In Example 1, the relative position information memory unit 25a for storing the relative position information between the sensitive area of the AEC photo pickup field and the FPD (FPD 32 in the case of X-ray imaging at the upright stand 31) is provided. The relative position information is referred to based on the positional information of the FPD 32, so that the positional information of the sensitive area of the AEC photo pickup field is calculated. The relative position information is referred to based on the positional information of the FPD 32, so that the positional information of the sensitive area of the AEC photo pickup field is calculated, so that the X-ray irradiation area is used for detecting the presence or absence of the AEC photo pickup field (not included in the X-ray irradiation area) in the control unit 28.

Example 2

Hereinafter, Example 2 of the present invention will be described with reference to the drawings. In Example 2, X-ray imaging is performed using the X-ray imaging apparatus 1 shown in FIG. 1 which is the same as the aforementioned Example 1, which will also be applied to the block diagram of FIG. 2.

Even in Example 1 described above, the X-ray imaging button 26C, the buzzer 27B, and the warning lamp 27C are provided, but in Example 2, functions of the X-ray imaging button 26C, the buzzer 27B, and the warning lamp 27C will also be described in detail. It should be noted that in FIG. 2, the display unit 27A, the buzzer 27B, and the warning lamp 27C are illustrated as separate structures, but a buzzer 27B and a warning lamp 27C are built in the display unit 27A. Of course, the display unit 27A, the buzzer 27B, and the warning lamp 27C may be configured separately from each other. The buzzer 27B and the warning lamp 27C in Example 2 correspond to the warning means in this example.

In Example 2, the control unit 28 has a function of the lighting field detection means for detecting the presence or absence of the AEC photo pickup field in which all areas of the sensitive area are not included in the X-ray irradiation area based on the positional information of the X-ray irradiation area and the sensitive area of the AEC photo pickup field (for automatic exposure). The control unit 28 in Example 2 corresponds to the lighting field detection means in this example.

In the same manner as in the aforementioned Example 1, in Example 2, the control unit 28 calculates the positional information of the X-ray irradiation area $V_I$ (see FIG. 4) based on the respective positional information of the X-ray tube 22, the collimator 29a, and the FPD (the FPD 32 in the case of X-ray imaging at the upright stand 31). With this, it is calculated which position of the FPD 32 the X-ray irradiation area $V_I$ is irradiated and set.

In the same manner as in the aforementioned Example 1, in Example 2, a relative position information memory unit 25a for storing the relative position information between the sensitive area of the AEC photo pickup field and the FPD (FPD 32 in the case of X-ray imaging at the upright stand 31) is provided. The control unit 28 calculates the positional information of the sensitive area of the AEC photo pickup field by referring to the relative position information based on the positional information of the FPD 32. Further, the control unit 28 detects the presence or absence of the AEC photo pickup field in which all areas of the sensitive area are not included in the X-ray irradiation area $V_I$ based on the positional information of the X-ray irradiation area $V_I$ and the sensitive area of the AEC photo pickup field.

In Example 2, when there exists an AEC photo pickup field not included in the X-ray irradiation area $V_I$, the control unit 28 outputs X-ray irradiation area mismatch information and sends the X-ray irradiation area mismatch information to the display unit 27A. When receiving the X-ray irradiation area mismatch information at the display unit 27A, the display unit 27A issues a warning with sound by the buzzer 27B or issues a warning with light by the warning lamp 27C. A warning may be issued by displaying an error message on the display unit 27A.

Although the display unit 27A is configured to issue a warning at the timing of receiving the X-ray irradiation area mismatch information, a warning may be issued at the timing when the X-ray imaging operation is performed by the operator. For example, a warning may be issued at the timing when an operator presses the X-ray imaging button 26C. In this case, a warning may be issued at the timing of heating the tube of the X-ray tube 22 by half pressing the X-ray imaging button 26C, or may issue a warning at the timing of preparing the X-ray irradiation by fully pressing of the X-ray imaging button 26C. That is, at the time of receiving the X-ray irradiation area mismatch information, for example, only the detection flag is set, and at the timing of pressing the X-ray imaging button 26C, a warning is issued based on the detection flag. When issuing a warning at the timing of preparing for X-ray irradiation with the full pressing of the X-ray imaging button 26C, the X-ray tube 22 does not irradiate X-rays.

As described above, in the aforementioned Example 1, a plurality of AEC photo pickup fields exist, but in Example 2, the present invention can also be applied to the case where there exists only one AEC photo pickup field. In the aforementioned Example 1, warning means such as the buzzer 27B and the warning lamp 27C is not essential, and in this Example 2, warning means such as the buzzer 27B and the warning lamp 27C is essential. According to the X-ray imaging apparatus according to Example 2 in the same manner as in the aforementioned Example 1, the control unit 28 detects the presence or absence of the AEC photo pickup field in which all areas of the sensitive area are not included in the X-ray irradiation area based on the positional information of the X-ray irradiation area and the sensitive area of and the AEC photo pickup field. As described in the function and effect of the aforementioned Example 1, the sensitive area decreases in the AEC photo pickup field not included in the X-ray irradiation area. In Example 2, in cases where there exists the AEC photo pickup field (i.e., an AEC photo pickup field in which the sensitive area is reduced) not included in the X-ray irradiation area, the warning means such as the aforementioned buzzer 27B and warning lamp 27C issues a warning. By issuing a warning to an operator by the warning means before X-ray imaging, it is understood that the X-ray irradiation area is deviated or missing from the sensitive area of the AEC photo pickup field before the X-ray imaging. Therefore, by readjusting the position of the subject M and/or the X-ray irradiation area by the operator, the appropriate X-ray total incident dose is incident on the AEC photo pickup field. Therefore, an appropriate automatic exposure control can be performed, which in turn can perform an appropriate X-ray imaging control, and the density (pixel value) of the X-ray captured image (X-ray image) obtained by imaging becomes constant. At this time, since the operator can recognize in advance that the positioning of imaging is different from usual, it is possible to correct when there is mispositioning of imaging, and the output/display position of the X-ray captured image (X-ray Image) does not change. Furthermore, by the readjustment, the X-ray output signal from the AEC photo pickup field is also the same as that in the prior art, and the multiplier as disclosed in Japanese Patent No. 5344807 may also become unnecessary. As a result, it is possible to appropriately perform an automatic exposure control and perform an X-ray imaging control appropriately with a simple structure.

As described above, the warning means may issue a warning with light by, for example, the warning lamp 27C, or a warning may be made with sound by, for example, the buzzer 27B. Further, the warning may be performed by combining both light and sound. For example, it may be configured such that the warning is normally performed with light (red light indicating a warning) and the warning is performed with sound at the stage before X-ray imaging.

Further, as described above, the warning means may issue a warning at the timing of performing the X-ray imaging operation by pressing the X-ray imaging button 26C, for example. That is, in cases where there exists an AEC photo pickup field not included in the X-ray irradiation area, at that time point (for example, at the time of receiving the X-ray irradiation area mismatch information), without issuing a warning by the warning means, for example, only a detection flag is set by lighting field detection means at the timing at which the X-ray imaging operation is performed (for example, timing at which the X-ray imaging button 26C is pressed), a warning is issued based on the detection flag. Also in this case, the warning means may issue a warning with light by, for example, the warning lamp 27C, or a warning may be made with sound by, for example, the buzzer 27B.

The present invention is not limited to the aforementioned Examples, and can be modified as follows.

(1) In each of the aforementioned Examples, the X-ray imaging apparatus is an apparatus as shown in FIG. 1. However, as long as it is an apparatus that performs X-ray imaging, it may be an apparatus that performs X-ray imaging only in a standing position, or it may be an apparatus that performs X-ray imaging only in a recumbent posture. Further, it may be an apparatus that performs X-ray imaging equipped with a tiltable table to which both the standing position and the recumbent posture can be applied.

(2) In each of the aforementioned Examples, the flat panel detector (FPD) is also used as the AEC detection unit. However, the AEC detection unit may be constituted by a photosensor tube such as a phototimer and the AEC detection unit may be installed on the incident side of the FPD. When installing the AEC detection unit on the incoming side of the FPD, in order to accurately obtain the positional information of the sensitive area of the AEC photo pickup field, it is preferable to store in advance the relative position information between the sensitive area of the AEC photo pickup field and the FPD and referring to the relative position information based on the positional information of the FPD, and the positional information of the sensitive area of the AEC lighting is calculated.

(3) In each of the aforementioned Examples, the flat panel type X-ray detector is exemplified as an example of the X-ray detection means. However, the X-ray detection means is not particularly limited as long as it is normally used such as an X-ray film and a CR.

(4) The aforementioned Example 1 and Example 2 may be combined. In the same manner as in the aforementioned Example 1, in cases where there exists a plurality of AEC photo pickup fields, when there exist one or more AEC photo pickup fields not included in the X-ray irradiation area, even when setting the corresponding photo pickup field to be unused, a warning may be given to an operator with the warning means (for example, the buzzer 27B or the warning lamp 27C) before the X-ray imaging. Then, the operator readjusts the position of the subject and the X-ray irradiation area so that an appropriate X-ray total incident dose is incident on the AEC photo pickup field which was set to be unused, and the AEC photo pickup field which was set to be unused is set to be usable.

(5) In the aforementioned Example 1, although AEC photo pickup fields other than the AEC photo pickup field set to be unused are selected and set from the AEC photo pickup field set (selected) by photo pickup field setting means (AEC photo pickup field selection button 26B in FIG. 2), it may not be necessary to configure the photo pickup field setting means with an input unit represented by an AEC photo pickup field selection button, etc. For example, the photo pickup field setting means may be composed of a central processing unit (CPU), etc., and the photo pickup field setting means may select and set the AEC photo pickup field other than the AEC photo pickup field which is set to be unused. In other words, the photo pickup field setting means may also serve as unused setting means.

DESCRIPTION OF REFERENCE SYMBOLS

1: X-ray imaging apparatus
22: X-ray tube
25a: relative position information memory unit
26B: AEC photo pickup field selection button
27B: warning lamp
27C: buzzer
28: control unit
29a: collimator
32, 42: flat panel type X-ray detector (FPD)
$V_C, V_L, V_R$: photo pickup field (AEC photo pickup field)
$V_I$: X-ray irradiation area
M: subject

The invention claimed is:

1. An X-ray imaging apparatus for performing X-ray imaging, comprising:
   X-ray irradiation means configured to irradiate an X-ray toward a subject;
   photo pickup field setting means configured to select a photo pickup field among a plurality of photo pickup fields for an automatic exposure and set the selected photo pickup field for use;
   lighting field detection means configured to detect whether at least a partial area of a sensitive area of a sensitive area of the selected photo pickup field is not included in an X-ray irradiation area based on positional information of the X-ray irradiation area irradiated by the X-ray irradiation means and the sensitive area of the photo pickup field; and
   unused setting means configured to set the selected photo pickup field to be unused in response to the lighting field detection means detecting that at least a partial area of the sensitive area of the selected photo pickup field is not included in the X-ray irradiation area.

2. The X-ray imaging apparatus as recited in claim 1, further comprising
   warning means configured to issue a warning when the photo pickup field not included in the X-ray irradiation area exists.

3. The X-ray imaging apparatus as recited in claim 1, further comprising:
   X-ray collimator means configured to limit an area irradiated by the X-ray irradiation means; and
   X-ray detection means configured to detect an X-ray that transmitted through the subject,
   wherein positional information of the X-ray irradiation area is calculated based on respective positional information of the X-ray irradiation means, the X-ray collimator means, and the X-ray detection means.

4. The X-ray imaging apparatus as recited in claim 1, further comprising:
   X-ray detection means configured to detect the X-ray that transmitted through the subject; and
   relative position information storage means configured to store relative position information between the sensitive area of the photo pickup field and the X-ray detection means,
   wherein the positional information of the sensitive area of the photo pickup field is calculated by referring to the relative position information based on the positional information of the X-ray detection means.

5. An X-ray imaging apparatus for performing X-ray imaging, comprising:
   X-ray irradiation means configured to irradiate an X-ray toward a subject;
   lighting field detection means configured to detect the existence of a photo pickup field in which one or more areas of a sensitive area are not included in an X-ray irradiation area based on positional information on the X-ray irradiation area irradiated by the X-ray irradiation means and the sensitive area of the photo pickup field for an automatic exposure; and
   warning means configured to issue a warning when the photo pickup field having one or more areas of the sensitive area not included in the X-ray irradiation area is detected to exist by the lighting field detection means.

6. The X-ray imaging apparatus as recited in claim 5, wherein the warning means issues a warning with light.

7. The X-ray imaging apparatus as recited in claim 5, wherein the warning means issues a warning with sound.

8. The X-ray imaging apparatus as recited in claim 5, wherein the warning means performs the warning at a timing when an X-ray imaging operation is performed.

9. An X-ray imaging method, comprising:
   irradiating an X-ray irradiation area;
   selecting a first photo pickup field among a plurality of photo pickup fields for an automatic exposure, wherein the first photo pickup field includes a corresponding sensitive area;
   detecting whether at least a portion of the sensitive area is not included in the X-ray irradiation area based on positional information of the X-ray irradiation area and the sensitive area, and setting the first photo pickup field to be unused in response to at least a portion of the sensitive area being not included in the X-ray irradiation area.

10. The X-ray imaging method as recited in claim 9, further comprising:
issuing a warning in response to at least a portion of the sensitive area being not included in the X-ray irradiation area.

11. The X-ray imaging method as recited in claim 10, wherein the warning is issued by a warning buzzer and/or a warning lamp.

12. The X-ray imaging method as recited in claim 9, further comprising:
limiting the X-ray irradiation area by an X-ray collimator; and
detecting an X-ray by a flat panel detector,
wherein the positional information of the X-ray irradiation area is calculated based on respective positional information of an X-ray source, the X-ray collimator, and the flat panel detector, and
wherein the X-ray source, the X-ray collimator, and the flat panel detector are movable relative to one another.

13. The X-ray imaging method as recited in claim 12, further comprising:
storing relative position information between the sensitive area of the photo pickup field and the flat panel detector, and
wherein the positional information of the sensitive area of the first photo pickup field is calculated by referring to the relative position information based on the positional information of the X-ray source.

14. The X-ray imaging method as recited in claim 12, wherein at least a portion of the X-ray irradiation area is improperly aligned with the flat panel detector, and the first photo pickup field is set to be unused.

15. An X-ray imaging apparatus for performing X-ray imaging, comprising:
X-ray irradiation means configured to irradiate an X-ray toward a subject;
photo pickup field setting means configured to select a photo pickup field among a plurality of photo pickup fields for an automatic exposure and set the selected photo pickup field for use;
lighting field detection means configured to detect whether all areas of a sensitive area of the selected photo pickup field are included in an X-ray irradiation area based on positional information of the X-ray irradiation area irradiated by the X-ray irradiation means and the sensitive area of the selected photo pickup field; and
unused setting means configured to set the selected photo pickup field to be unused in response to one or more areas of the sensitive area of the selected photo pickup field being detected by the lighting field detection means as being not included in the X-ray irradiation area.

* * * * *